United States Patent [19]

McKinnie et al.

[11] Patent Number: 4,537,724
[45] Date of Patent: Aug. 27, 1985

[54] ALKANOYLOXYBENZENESULFONATE SALT PRODUCTION

[75] Inventors: Bonnie G. McKinnie; Gene C. Robinson, both of Baton Rouge, La.

[73] Assignee: Ethyl Corporation, Richmond, Va.

[21] Appl. No.: 493,452

[22] Filed: May 11, 1983

[51] Int. Cl.³ ............... C07C 143/90; C11D 1/28
[52] U.S. Cl. .................................................. 260/400
[58] Field of Search ............... 260/400, 402; 560/142, 560/234, 109, 217

[56] References Cited

U.S. PATENT DOCUMENTS

| | | | |
|---|---|---|---|
| 2,337,924 | 12/1943 | Platz et al. | 560/142 |
| 3,023,183 | 2/1962 | Nelson | 260/400 X |
| 3,636,016 | 1/1972 | McGuire | 260/402 |
| 4,285,971 | 8/1981 | Muntwyler | 560/109 |

*Primary Examiner*—Helen M. S. Sneed
*Attorney, Agent, or Firm*—Donald L. Johnson; John F. Sieberth; Joseph D. Odenweller

[57] ABSTRACT

An alkali metal or an alkaline earth metal salt of an acyloxybenzenesulfonate of the formula:

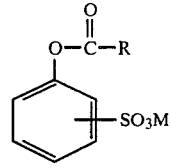

wherein R is a hydrocarbyl group containing up to 30 carbon atoms selected from alkyl, alkenyl, cycloalkyl, aryl, aralkyl and M is an alkali metal or an alkaline earth metal is prepared by reacting at elevated temperature the corresponding hydroxybenzene sulfonate salt of the formula:

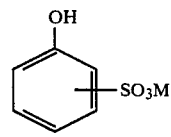

with an aryl ester of the formula:

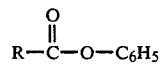

wherein R is as defined above.

20 Claims, No Drawings

ALKANOYLOXYBENZENESULFONATE SALT PRODUCTION

TECHNICAL FIELD

This invention relates to the production of alkali metal and alkaline earth metal salts of certain acyloxybenzenesulfonates, and more particularly to the manufacture of these salts by reaction between the corresponding salts of hydroxybenzenesulfonic acid and aryl esters. The acyloxybenzenesulfonate salts of the present invention have many applications. For example, they are used in the textile industry as activators for the peroxide bleaching of fabrics and as dyeing assistants in the dyeing of acrylic fibers.

THE INVENTION

In a specific embodiment, and by way of illustration, the present invention contemplates the production of sodium 4-nonanoyloxybenzenesulfonate in accordance with the following equation:

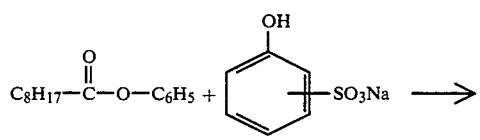

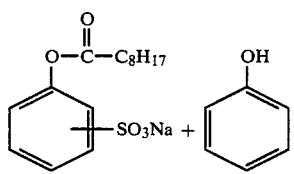

In other embodiments, the invention contemplates the production of alkali metal and alkaline earth metal salts of acyloxybenzenesulfonates of the formula:

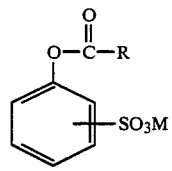
(I)

wherein R is a hydrocarbyl radical containing up to 30 carbon atoms and is selected from alkyl, alkenyl, cycloalkyl, aryl, aralkyl and M is an alkali metal or an alkaline earth metal by reacting at elevated temperature the corresponding hydroxybenzene sulfonate salt of the formula:

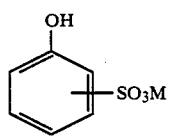
(II)

with an aryl ester of the formula:

$$R-\overset{O}{\underset{\|}{C}}-O-C_6H_5 \quad (III)$$

wherein R and M are as defined above.

The aryl esters of the invention are known to the art as are methods for their preparation. For example, U.S. Pat. No. 2,467,206, incorporated herein by reference, discloses the synthesis of aryl esters of the formula acylOR, R representing an aryl group attached to phenolic hydroxyl in phenol by heating an organic compound containing non-aromatic olefinic unsaturation with carbon monoxide and a phenol at elevated temperature and pressure in the presence of a catalyst containing, as an essential ingredient, cobalt or nickel.

Aelony, "Direct Esterification of Phenols with Higher Fatty Acids", *Journal of the American Oil Chemists' Society*, 32, 170–172 (1955), discloses a method of preparing fatty acid esters of many monohydric and dihydric phenols by direct esterification of the phenols with higher fatty acids at reaction temperatures between 115°–290° C., optionally in the presence of catalysts such as sulfuric acid, phosphoric acid, zinc stearate, lead stearate and triphenyl phosphite.

The hydroxybenzenesulfonate salts which may be used in accordance with this invention are salts of the formula:

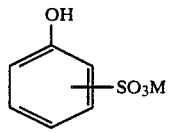

wherein M is an alkali metal or an alkaline earth metal. The metal sulfonate functional group can be bonded to any of the aromatic carbon atoms either ortho-, meta- or para- to the hydroxyl group in the ring. The hydroxybenzenesulfonate salts of the present invention are known compounds and can be prepared by methods known to the art, such as, for example, by treating phenol with sulfuric acid in the presence of boron fluoride at elevated temperature as described by R. J. Thomas, et al., "Sulfonation and Nitration Reaction Promoted by Boron Fluoride", *Industrial and Engineering Chemistry*, 32, 408–410 (1940).

Representative examples of hydroxybenzenesulfonate salt reactants are:
sodium 2-hydroxybenzenesulfonate;
sodium 3-hydroxybenzenesulfonate;
sodium 4-hydroxybenzenesulfonate;
potassium 2-hydroxybenzenesulfonate;
potassium 3-hydroxybenzenesulfonate;
potassium 4-hydroxybenzenesulfonate;
calcium 2-hydroxybenzenesulfonate;
calcium 3-hydroxybenzenesulfonate;
calcium 4-hydroxybenzenesulfonate.

Representative examples of acyl ester reactants which may be used in the present invention are:
phenyl formate;
phenyl acetate;
phenyl propionate;
phenyl butyrate;
phenyl pentanoate;
phenyl hexanoate;
phenyl heptanoate;
phenyl octanoate;
phenyl nonanoate;
phenyl decanoate;
phenyl undecanoate;
phenyl dodecanoate;
phenyl tridecanoate;

phenyl tetradecanoate;
phenyl pentadecanoate;
phenyl hexadecanoate;
phenyl heptadecanoate;
phenyl octadecanoate;
phenyl nonadecanoate;
phenyl eicosanoate;
phenyl heneicosanoate;
phenyl docosanoate;
phenyl tricosanoate;
phenyl tetracosanoate;
phenyl pentacosanoate;
phenyl hexacosanoate;
phenyl heptacosanoate;
phenyl octacosanoate;
phenyl nonacosanoate;
phenyl triacontanoate;
phenyl acrylate;
phenyl 2-butenoate;
phenyl 2-pentenoate;
phenyl 3-pentenoate;
phenyl 2-hexenoate;
phenyl 3-hexenoate;
phenyl 4-hexenoate;
phenyl 5-hexenoate;
phenyl 2-heptenoate;
phenyl 3-heptenoate;
phenyl 4-heptenoate;
phenyl 5-heptenoate;
phenyl 6-heptenoate;
phenyl 2-octenoate;
phenyl 3-octenoate;
phenyl 4-octenoate;
phenyl 2-nonenoate;
phenyl 3-nonenoate;
phenyl 4-nonenoate;
phenyl 2-decenoate;
phenyl 3-decenoate;
phenyl 4-decenoate;
phenyl 2-undecenoate;
phenyl 3-undecenoate;
phenyl 4-undecenoate;
phenyl 2-dodecenoate;
phenyl 3-dodecenoate;
phenyl 4-dodecenoate;
phenyl 2-tridecenoate;
phenyl 3-tridecenoate;
phenyl 4-tridecenoate;
phenyl 2-tetradecenoate;
phenyl 3-tetradecenoate;
phenyl 4-tetradecenoate;
phenyl 2-pentadecenoate;
phenyl 3-pentadecenoate;
phenyl 4-pentadecenoate;
phenyl 2-hexadecenoate;
phenyl 3-hexadecenoate;
phenyl 4-hexadecenoate;
phenyl 2-heptadecenoate;
phenyl 3-heptadecenoate;
phenyl 4-heptadecenoate;
phenyl 2-octadecenoate;
phenyl 3-octadecenoate;
phenyl 4-octadecenoate;
phenyl 2-nonadecenoate;
phenyl 3-nonadecenoate;
phenyl 4-nonadecenoate;
phenyl 2-eicosenoate;
phenyl 3-eicosenoate;
phenyl 4-eicosenoate;
phenyl 2-heneicosenoate;
phenyl 3-heneicosenoate;
phenyl 4-heneicosenoate;
phenyl 2-docosenoate;
phenyl 3-docosenoate;
phenyl 4-docosenoate;
phenyl 2-tricosenoate;
phenyl 3-tricosenoate;
phenyl 4-tricosenoate;
phenyl 2-tetracosenoate;
phenyl 3-tetracosenoate;
phenyl 4-tetracosenoate;
phenyl 2-pentacosenoate;
phenyl 3-pentacosenoate;
phenyl 4-pentacosenoate;
phenyl 2-hexacosenoate;
phenyl 3-hexacosenoate;
phenyl 4-hexacosenoate;
phenyl 2-heptacosenoate;
phenyl 3-heptacosenoate;
phenyl 4-heptacosenoate;
phenyl 2-octacosenoate;
phenyl 3-octacosenoate;
phenyl 4-octacosenoate;
phenyl 2-nonacosenoate;
phenyl 3-nonacosenoate;
phenyl 4-nonacosenoate;
phenyl 2-triacontenoate;
phenyl 3-triacontenoate;
phenyl 4-triacontenoate;
phenyl benzoate;
phenyl phenylacetate;
phenyl phenylpropionate;
phenyl phenylbutyrate;
phenyl phenylpentanoate;
phenyl phenylhexanoate;
phenyl phenylheptanoate;
phenyl phenyloctanoate;
phenyl phenylnonanoate;
phenyl phenyldecanoate;
phenyl phenylundecanoate;
phenyl phenyldodecanoate;
phenyl phenyltridecanoate;
phenyl phenyltetradecanoate;
phenyl phenylpentadecanoate;
phenyl phenylhexadecanoate;
phenyl phenylheptadecanoate;
phenyl phenyloctadecanoate;
phenyl phenylnonadecanoate;
phenyl phenyleicosanoate;
phenyl naphthoate;
phenyl cyclobutanecarboxylate;
phenyl cyclopentanecarboxylate;
phenyl cyclohexanecarboxylate;
phenyl cycloheptanecarboxylate;
phenyl cyclooctanecarboxylate;
phenyl cyclononanecarboxylate;
phenyl cyclodecanecarboxylate;
phenyl cycloundecanecarboxylate;
phenyl cyclododecanecarboxylate;
phenyl cyclotridecanecarboxylate;
phenyl cyclotetradecanecarboxylate;
phenyl cyclopentadecanecarboxylate;
phenyl cyclohexadecanecarboxylate;
phenyl cycloheptadecanecarboxylate;
phenyl cyclooctadecanecarboxylate;
phenyl cyclononadecanecarboxylate;

phenyl cycloeicosanecarboxylate;
phenyl 2-methylbenzoate;
phenyl 3-ethylbenzoate;
phenyl 2,3-dimethylbenzoate;
phenyl 2-propylbenzoate;
phenyl 2-isopropylbenzoate;
phenyl 2-t-butylbenzoate;
phenyl 4-octylbenzoate;
phenyl 4-decylbenzoate;
phenyl 4-dodecylbenzoate;
phenyl 4-pentadecylbenzoate;
phenyl 4-octadecylbenzoate;
mixtures thereof and the like.

Representative examples of the acyloxybenzenesulfonate salt products of the present process are:
benzenesulfonic acid, 2-hydroxy-,formate,sodium salt;
benzenesulfonic acid, 2-hydroxy-,formate,potassium salt;
benzenesulfonic acid, 2-hydroxy-,formate,calcium salt;
benzenesulfonic acid, 3-hydroxy-,formate,sodium salt;
benzenesulfonic acid, 3-hydroxy-,formate,potassium salt;
benzenesulfonic acid, 3-hydroxy-,formate,calcium salt;
benzenesulfonic acid, 4-hydroxy-,formate,sodium salt;
benzenesulfonic acid, 4-hydroxy-,formate,potassium salt;
benzenesulfonic acid, 4-hydroxy-,formate,calcium salt;
benzenesulfonic acid, 2-hydroxy-,acetate,sodium salt;
benzenesulfonic acid, 2-hydroxy-,acetate,potassium salt;
benzenesulfonic acid, 2-hydroxy-,acetate,calcium salt;
benzenesulfonic acid, 3-hydroxy-,acetate,sodium salt;
benzenesulfonic acid, 3-hydroxy-,acetate,potassium salt;
benzenesulfonic acid, 3-hydroxy-,acetate,calcium salt;
benzenesulfonic acid, 4-hydroxy-,acetate,sodium salt;
benzenesulfonic acid, 4-hydroxy-,acetate,potassium salt;
benzenesulfonic acid, 4-hydroxy-,acetate,calcium salt
benzenesulfonic acid, 2-hydroxy-,propionate,sodium salt;
benzenesulfonic acid, 2-hydroxy-,propionate,potassium salt;
benzenesulfonic acid, 2-hydroxy-,propionate,calcium salt;
benzenesulfonic acid, 3-hydroxy-,propionate,sodium salt;
benzenesulfonic acid, 3-hydroxy-,propionate,potassium salt;
benzenesulfonic acid, 3-hydroxy-,propionate,calcium salt;
benzenesulfonic acid, 4-hydroxy-,propionate,sodium salt;
benzenesulfonic acid, 4-hydroxy-,propionate,potassium salt;
benzenesulfonic acid, 4-hydroxy-,propionate,calcium salt;
benzenesulfonic acid, 4-hydroxy-,butyrate,sodium salt;
benzenesulfonic acid, 4-hydroxy-,pentanoate,sodium salt;
benzenesulfonic acid, 4-hydroxy-,hexanoate,sodium salt;
benzenesulfonic acid, 2-hydroxy-,heptanoate,sodium salt;
benzenesulfonic acid, 2-hydroxy-,heptanoate,potassium salt;
benzenesulfonic acid, 2-hydroxy-,heptanoate,calcium salt;
benzenesulfonic acid, 3-hydroxy-,heptanoate,sodium salt;
benzenesulfonic acid, 3-hydroxy-,heptanoate,potassium salt;
benzenesulfonic acid, 3-hydroxy-,heptanoate,calcium salt;
benzenesulfonic acid, 4-hydroxy-,heptanoate,sodium salt;
benzenesulfonic acid, 4-hydroxy-,heptanoate,potassium salt;
benzenesulfonic acid, 4-hydroxy-,heptanoate,calcium salt;
benzenesulfonic acid, 4-hydroxy-,octanoate,sodium salt;
benzenesulfonic acid, 2-hydroxy-,nonanoate,sodium salt;
benzenesulfonic acid, 2-hydroxy-,nonanoate,potassium salt;
benzenesulfonic acid, 2-hydroxy-,nonanoate,calcium salt;
benzenesulfonic acid, 3-hydroxy-,nonanoate,sodium salt;
benzenesulfonic acid, 3-hydroxy-,nonanoate,potassium salt;
benzenesulfonic acid, 3-hydroxy-,nonanoate,calcium salt;
benzenesulfonic acid, 4-hydroxy-,nonanoate,sodium salt;
benzenesulfonic acid, 4-hydroxy-,nonanoate,potassium salt;
benzenesulfonic acid, 4-hydroxy-,nonanoate,calcium salt;
benzenesulfonic acid, 4-hydroxy-,decanoate,sodium salt;
benzenesulfonic acid, 4-hydroxy-,undecanoate,sodium salt;
benzenesulfonic acid, 4-hydroxy-,dodecanoate,sodium salt;
benzenesulfonic acid, 4-hydroxy-,tridecanoate,sodium salt;
benzenesulfonic acid, 4-hydroxy-,tetradecanoate,sodium salt;
benzenesulfonic acid, 4-hydroxy-,pentadecanoate,sodium salt;
benzenesulfonic acid, 4-hydroxy-,hexadecanoate,sodium salt;
benzenesulfonic acid, 4-hydroxy-,heptadecanoate,sodium salt;
benzenesulfonic acid, 4-hydroxy-,octadecanoate,sodium salt;
benzenesulfonic acid, 4-hydroxy-,nonadecanoate,sodium salt;
benzenesulfonic acid, 4-hydroxy-,eicosanoate,sodium salt;
benzenesulfonic acid, 4-hydroxy-,heneicosanoate,sodium salt;
benzenesulfonic acid, 4-hydroxy-,docosanoate,sodium salt;
benzenesulfonic acid, 4-hydroxy-,tricosanoate,sodium salt;
benzenesulfonic acid, 4-hydroxy-,tetracosanoate,sodium salt;
benzenesulfonic acid, 4-hydroxy-,pentacosanoate,sodium salt;
benzenesulfonic acid, 4-hydroxy-,hexacosonoate,sodium salt;
benzenesulfonic acid, 4-hydroxy-,heptacosanoate,sodium salt;

benzenesulfonic acid, 4-hydroxy-,octacosanoate,sodium salt;
benzenesulfonic acid, 4-hydroxy-,nonacosonoate,-sodium salt;
benzenesulfonic acid, 4-hydroxy-,triacontanoate,-sodium salt;
benzenesulfonic acid, 4-hydroxy-,acrylate,sodium salt;
benzenesulfonic acid, 4-hydroxy-,but-2-enoate,sodium salt;
benzenesulfonic acid, 4-hydroxy-,but-2-enoate,potassium salt;
benzenesulfonic acid, 4-hydroxy-,but-2-enoate,calcium salt;
benzenesulfonic acid, 4-hydroxy-,pent-2-enoate,sodium salt;
benzenesulfonic acid, 4-hydroxy-,pent-2-enoate,potassium salt;
benzenesulfonic acid, 4-hydroxy-,pent-2-enoate,calcium salt;
benzenesulfonic acid, 4-hydroxy-,pent-3-enoate,sodium salt;
benzenesulfonic acid, 4-hydroxy-,pent-3-enoate,potassium salt;
benzenesulfonic acid, 4-hydroxy-,pent-3-enoate,calcium salt;
benzenesulfonic acid, 4-hydroxy-,hex-2-enoate,sodium salt;
benzenesulfonic acid, 4-hydroxy-,hex-3-enoate,sodium salt;
benzenesulfonic acid, 4-hydroxy-,hex-4-enoate,sodium salt;
benzenesulfonic acid, 4-hydroxy-,hex-5-enoate,sodium salt;
benzenesulfonic acid, 4-hydroxy-,hept-2-enoate,sodium salt;
benzenesulfonic acid, 4-hydroxy-,hept-3-enoate,sodium salt;
benzenesulfonic acid, 4-hydroxy-,hept-4-enoate,sodium salt;
benzenesulfonic acid, 4-hydroxy-,hept-5-enoate,sodium salt;
benzenesulfonic acid, 4-hydroxy-,hept-6-enoate,sodium salt;
benzenesulfonic acid, 4-hydroxy-,oct-2-enoate,sodium salt;
benzenesulfonic acid, 4-hydroxy-,oct-3-enoate,sodium salt;
benzenesulfonic acid, 4-hydroxy-,oct-4-enoate,sodium salt;
benzenesulfonic acid, 4-hydroxy-,non-2-enoate,sodium salt;
benzenesulfonic acid, 4-hydroxy-,non-3-enoate,sodium salt;
benzenesulfonic acid, 4-hydroxy-,non-4-enoate,sodium salt;
benzenesulfonic acid, 4-hydroxy-,dec-2-enoate,sodium salt;
benzenesulfonic acid, 4-hydroxy-,dec-3-enoate,sodium salt;
benzenesulfonic acid, 4-hydroxy-,dec-4-enoate,sodium salt;
benzenesulfonic acid, 4-hydroxy-,undec-2-enoate,-sodium salt;
benzenesulfonic acid, 4-hydroxy-,undec-3-enoate,-sodium salt;
benzenesulfonic acid, 4-hydroxy-,undec-4-enoate,-sodium salt;
benzenesulfonic acid, 4-hydroxy-,dodec-2-enoate,-sodium salt;
benzenesulfonic acid, 4-hydroxy-,dodec-3-enoate,-sodium salt;
benzenesulfonic acid, 4-hydroxy-,dodec-4-enoate,-sodium salt;
benzenesulfonic acid, 4-hydroxy-,tridec-2-enoate,-sodium salt;
benzenesulfonic acid, 4-hydroxy-,tridec-3-enoate,-sodium salt;
benzenesulfonic acid, 4-hydroxy-,tridec-4-enoate,-sodium salt;
benzenesulfonic acid, 4-hydroxy-,tetradec-2-enoate,-sodium salt;
benzenesulfonic acid, 4-hydroxy-,tetradec-3-enoate,-sodium salt;
benzenesulfonic acid, 4-hydroxy-,tetradec-4-enoate,-sodium salt;
benzenesulfonic acid, 4-hydroxy-,pentadec-2-enoate,-sodium salt;
benzenesulfonic acid, 4-hydroxy-,pentadec-3-enoate,-sodium salt;
benzenesulfonic acid, 4-hydroxy-,pentadec-4-enoate,-sodium salt;
benzenesulfonic acid, 4-hydroxy-,hexadec-2-enoate,-sodium salt;
benzenesulfonic acid, 4-hydroxy-,hexadec-3-enoate,-sodium salt;
benzenesulfonic acid, 4-hydroxy-,hexadec-4-enoate,-sodium salt;
benzenesulfonic acid, 4-hydroxy-,heptadec-2-enoate,-sodium salt;
benzenesulfonic acid, 4-hydroxy-,heptadec-3-enoate,-sodium salt;
benzenesulfonic acid, 4-hydroxy-,heptadec-4-enoate,-sodium salt;
benzenesulfonic acid, 4-hydroxy-,octadec-2-enoate,-sodium salt;
benzenesulfonic acid, 4-hydroxy-,octadec-3-enoate,-sodium salt;
benzenesulfonic acid, 4-hydroxy-,octadec-4-enoate,-sodium salt;
benzenesulfonic acid, 4-hydroxy-,nonadec-2-enoate,-sodium salt;
benzenesulfonic acid, 4-hydroxy-,nonadec-3-enoate,-sodium salt;
benzenesulfonic acid, 4-hydroxy-,nonadec-4-enoate,-sodium salt;
benzenesulfonic acid, 4-hydroxy-,eicos-2-enoate,sodium salt;
benzenesulfonic acid, 4-hydroxy-,eicos-3-enoate,sodium salt;
benzenesulfonic acid, 4-hydroxy-,eicos-4-enoate,sodium salt;
benzenesulfonic acid, 4-hydroxy-,heneicos-2-enoate,-sodium salt;
benzenesulfonic acid, 4-hydroxy-,heneicos-3-enoate,-sodium salt;
benzenesulfonic acid, 4-hydroxy-,heneicos-4-enoate,-sodium salt;
benzenesulfonic acid, 4-hydroxy-,docos-2-enoate,-sodium salt;
benzenesulfonic acid, 4-hydroxy-,docos-3-enoate,-sodium salt;
benzenesulfonic acid, 4-hydroxy-,docos-4-enoate,-sodium salt;
benzenesulfonic acid, 4-hydroxy-,tricos-2-enoate,-sodium salt;

benzenesulfonic acid, 4-hydroxy-,tricos-3-enoate,-sodium salt;
benzenesulfonic acid, 4-hydroxy-,tricos-4-enoate,-sodium salt;
benzenesulfonic acid, 4-hydroxy-,tetracos-2-enoate,-sodium salt;
benzenesulfonic acid, 4-hydroxy-,tetracos-3-enoate,-sodium salt;
benzenesulfonic acid, 4-hydroxy-,tetracos-4-enoate,-sodium salt;
benzenesulfonic acid, 4-hydroxy-,pentacos-2-enoate,-sodium salt;
benzenesulfonic acid, 4-hydroxy-,pentacos-3-enoate,-sodium salt;
benzenesulfonic acid, 4-hydroxy-,pentacos-4-enoate,-sodium salt;
benzenesulfonic acid, 4-hydroxy-,hexacos-2-enoate,-sodium salt;
benzenesulfonic acid, 4-hydroxy-,hexacos-3-enoate,-sodium salt;
benzenesulfonic acid, 4-hydroxy-,hexacos-4-enoate,-sodium salt;
benzenesulfonic acid, 4-hydroxy-,heptacos-2-enoate,-sodium salt;
benzenesulfonic acid, 4-hydroxy-,heptacos-3-enoate,-sodium salt;
benzenesulfonic acid, 4-hydroxy-,heptacos-4-enoate,-sodium salt;
benzenesulfonic acid, 4-hydroxy-,octacos-2-enoate,-sodium salt;
benzenesulfonic acid, 4-hydroxy-,octacos-3-enoate,-sodium salt;
benzenesulfonic acid, 4-hydroxy-,octacos-4-enoate,-sodium salt;
benzenesulfonic acid, 4-hydroxy-,nonacos-2-enoate,-sodium salt;
benzenesulfonic acid, 4-hydroxy-,nonacos-3-enoate,-sodium salt;
benzenesulfonic acid, 4-hydroxy-,nonacos-4-enoate,-sodium salt;
benzenesulfonic acid, 4-hydroxy-,triacont-2-enoate,-sodium salt;
benzenesulfonic acid, 4-hydroxy-,triacont-3-enoate,-sodium salt;
benzenesulfonic acid, 4-hydroxy-,triacont-4-enoate,-sodium salt;
benzenesulfonic acid, 4-hydroxy-,benzoate,sodium salt;
benzenesulfonic acid, 4-hydroxy-,benzoate,potassium salt;
benzenesulfonic acid, 4-hydroxy-,benzoate,calcium salt;
benzenesulfonic acid, 4-hydroxy-,phenylacetate,sodium salt;
benzenesulfonic acid, 4-hydroxy-,phenylacetate,potassium salt;
benzenesulfonic acid, 4-hydroxy-,phenylacetate,calcium salt;
benzenesulfonic acid, 4-hydroxy-,phenylpropionate,-sodium salt;
benzenesulfonic acid, 4-hydroxy-,phenylpropionate,-potassium salt;
benzenesulfonic acid, 4-hydroxy-,phenylpropionate,calcium salt;
benzenesulfonic acid, 4-hydroxy-,phenylbutyrate,-sodium salt;
benzenesulfonic acid, 4-hydroxy-,phenylpentanoate,-sodium salt;
benzenesulfonic acid, 4-hydroxy-,phenylhexanoate,-sodium salt;
benzenesulfonic acid, 4-hydroxy-,phenylheptanoate,-sodium salt;
benzenesulfonic acid, 4-hydroxy-,phenyloctanoate,-sodium salt;
benzenesulfonic acid, 4-hydroxy-,phenylnonanoate,-sodium salt;
benzenesulfonic acid, 4-hydroxy-,phenyldecanoate,-sodium salt;
benzenesulfonic acid, 4-hydroxy-,phenylundecanoate,-sodium salt;
benzenesulfonic acid, 4-hydroxy-,phenyldodecanoate,-sodium salt;
benzenesulfonic acid, 4-hydroxy-,phenyltridecanoate,-sodium salt;
benzenesulfonic acid, 4-hydroxy-,phenyltetradecanoate,sodium salt;
benzenesulfonic acid, 4-hydroxy-,phenylpentadecanoate,sodium salt;
benzenesulfonic acid, 4-hydroxy-,phenylhexadecanoate,sodium salt;
benzenesulfonic acid, 4-hydroxy-,phenylheptadecanoate,sodium salt;
benzenesulfonic acid, 4-hydroxy-,phenyloctadecanoate,sodium salt;
benzenesulfonic acid, 4-hydroxy-,phenylnonadecanoate,sodium salt;
benzenesulfonic acid, 4-hydroxy-,phenyleicosanoate,-sodium salt;
benzenesulfonic acid, 4-hydroxy-,naphthoate,sodium salt;
benzenesulfonic acid, 4-hydroxy-,naphthoate,potassium salt;
benzenesulfonic acid, 4-hydroxy-,naphthoate,calcium salt;
benzenesulfonic acid, 4-hydroxy-,cyclobutanecarboxylate,sodium salt;
benzenesulfonic acid, 4-hydroxy-,cyclopentanecarboxylate,sodium salt;
benzenesulfonic acid, 4-hydroxy-,cyclohexanecarboxylate,sodium salt;
benzenesulfonic acid, 4-hydroxy-,cycloheptanecarboxylate,sodium salt;
benzenesulfonic acid, 4-hydroxy-,cyclooctanecarboxylate,sodium salt;
benzenesulfonic acid, 4-hydroxy-,cyclononanecarboxylate,sodium salt;
benzenesulfonic acid, 4-hydroxy-,cyclodecanecarboxylate,sodium salt;
benzenesulfonic acid, 4-hydroxy-,cycloundecanecarboxylate,sodium salt;
benzenesulfonic acid, 4-hydroxy-,cyclododecanecarboxylate,sodium salt;
benzenesulfonic acid, 4-hydroxy-,cyclotridecanecarboxylate,sodium salt;
benzenesulfonic acid, 4-hydroxy-,cyclotetradecanecarboxylate, sodium salt;
benzenesulfonic acid, 4-hydroxy-,cyclopentadecanecarboxylate, sodium salt;
benzenesulfonic acid, 4-hydroxy-,cyclohexadecanecarboxylate, sodium salt;
benzenesulfonic acid, 4-hydroxy-,cycloheptadecanecarboxylate, sodium salt;
benzenesulfonic acid, 4-hydroxy-,cyclooctadecanecarboxylate, sodium salt;
benzenesulfonic acid, 4-hydroxy-,cyclononadecanecarboxylate, sodium salt;
benzenesulfonic acid, 4-hydroxy-,cycloeicosanecarboxylate,sodium salt;

benzenesulfonic acid, 4-hydroxy-,2-methylbenzoate,-sodium salt;
benzenesulfonic acid, 4-hydroxy-,3-ethylbenzoate,-sodium salt;
benzenesulfonic acid, 4-hydroxy-,2,3-dimethylbenzoate,sodium salt;
benzenesulfonic acid, 4-hydroxy-,2-propylbenzoate,-sodium salt;
benzenesulfonic acid, 4-hydroxy-,2-isopropylbenzoate,-sodium salt;
benzenesulfonic acid, 4-hydroxy-,2-t-butylbenzoate,-sodium salt;
benzenesulfonic acid, 4-hydroxy-,4-octylbenzoate,-sodium salt;
benzenesulfonic acid, 4-hydroxy-,4-decylbenzoate,-sodium salt;
benzenesulfonic acid, 4-hydroxy-,4-dodecylbenzoate,-sodium salt;
benzenesulfonic acid, 4-hydroxy-,4-pentadecylbenzoate,sodium salt;
benzenesulfonic acid, 4-hydroxy-,4-octadecylbenzoate,-sodium salt;
and mixtures thereof.

The process of the invention is carried out by heating the mixture of aryl ester and the alkali metal or alkaline earth metal salt of hydroxybenzenesulfonic acid in a suitable reaction vessel. In general, the process is carried out at a temperature of from about 200° to about 350° C., more preferably, about 250° to 325° C.

Although not required, it is preferred that the process be carried out under substantially anhydrous conditions, and accordingly, the components of the reaction system are brought together and maintained under a substantially dry, inert atmosphere. It is not necessary, however, that the reagents used in the process be anhydrous before they are combined as any water present in the reagents can be removed therefrom by conventional techniques, such as, for example, by azeotropic distillation of the combined reagents using an organic solvent such as hexane, octane, toluene, xylenes, and the like.

Typically, oxygen-containing compounds other than the desired acyloxybenzenesulfonate salts are produced by the process of the invention. Phenol and disodium phenol-2,4-disulfonate are the primary by-products formed by the reaction. However, as set forth in the examples, the yield of acyloxybenzenesulfonate salt may be as high as 90 weight percent and above. Removal of phenol from the reaction mixture is readily effected by distilling as rapidly as it is formed. Since the reaction is an equilibrium reaction, removal of the phenol helps to drive the reaction to completion. In general, the use of a fractionating column is not necessary. However, in those instances where an aryl ester reactant used in the process has a boiling point close to that of phenol, the use of a fractionating column is desirable.

The relative proportion of reactants employed by the reaction may be the stoichiometrically required quantities although other proportions may be employed if desired. It is preferred to use an excess of aryl ester in the reaction since the use of greater than stoichiometric quantities of ester also serves to drive the reaction to completion. Excellent results are obtained when the mole ratio of aryl ester to hydroxybenzenesulfonate salt is about 1.25 to 5:1.

Typically, the reaction is carried out at atmospheric pressure, however, higher pressures up to 1000 psig, or higher, can be used if desired. The maximum pressure is limited only by the strength of the retaining vessel. However, when aryl esters having boiling points greater than approximately 350° C. are used in the process of the invention, the reaction may be carried out at subatmospheric pressures to facilitate distillation of by-product phenol.

If desired, an inert liquid may be employed as a reaction medium. However, the reaction may be conducted satisfactorily in the absence of any added medium, especially, if an excess of aryl ester reactant is used in the process. If a solvent is used, it is advantageous, but not necessary, that the solvent have a boiling point higher than the by-product phenol produced by the process and lower than the aryl ester reactant. In this manner, it is possible to distill off substantially all of the unwanted phenol while preventing the aryl ester reactant from distilling off during the reaction. This allows distillation to be carried out at atmospheric pressure when a higher boiling aryl ester is used in the process and thus avoids conducting the reaction at subatmospheric pressures which would otherwise be necessary in the absence of a solvent. Examples of solvents which may be used in the process include the chlorinated benzenes, the chlorinated toluenes, higher boiling alkanes such as undecane, tetradecane, hexadecane, mineral oil and mixtures of higher boiling linear and branched alkanes. Additionally, aprotic solvents such as triglyme, tetraglyme, 1,2-diethoxyethane and dipolar aprotic solvents such as N,N-dimethylacetamide, tetramethylene sulfone, N-methylpyrrolidinone and like materials may also be used.

The acyloxybenzenesulfonate salts produced by the process are easily separated from unreacted aryl ester and solvent which remain after the removal of by-product phenol. Preferably, the reaction mixture is filtered and the solid product washed free of aryl ester and solvent by the use of a low boiling solvent such as heptane, toluene, dichloromethane or diethyl ether. The low boiling solvent is then removed by evaporation from the solid product. Alternatively, the acyloxybenzenesulfonate salt product may be separated from the reaction mixture by dissolving it in water in which the reaction solvent and aryl ester reagents are generally insoluble, separating the organic and aqueous phases thus formed and separating the acyloxybenzenesulfonate salt from the aqueous phase by known techniques such as crystallization or spray drying.

The process of this invention will be still further apparent by the following illustrative examples.

EXAMPLE 1

Preparation of Phenyl Heptanoate

Heptanoic acid (180.9 g; 1.39 mol), phenol (180.69 g; 1.92 mol), toluene (216.5; 2.35 mol) and sulfuric acid (5.04 g; 0.0514 mol) were charged to a 2-liter, 3-necked round bottom flask equipped with a thermometer, a magnetic stirrer and an 8" Vigreux column equipped with a Dean-Stark trap. The reaction mixture was heated to 131° C. and maintained at that temperature for five hours to give 74 weight percent phenyl heptanoate. The reaction product was washed once with a solution of 0.08 mol $Na_2CO_3$ in 4.5 mol water. Phase separation occurred after approximately 20 minutes. The organic layer was fractionally distilled at atmospheric pressure using a 20-plate Oldershaw column to remove phenol and toluene. The remaining liquid was then distilled through a 10-plate Oldershaw column at 50 torr to give a center cut fraction of 154.4 g (54% yield) of pure phenyl heptanoate.

EXAMPLE 2

Preparation of benzenesulfonic acid, 4-hydroxynonanoate, sodium salt

A 1-liter, 3-necked round bottom flask equipped with a mechanical stirrer, thermocouple well and a Dean-Stark trap was charged with sodium 4-hydroxybenzenesulfonate dihydrate (160 g; 0.670 mol), hexadecane (102 g), and octane (166 g). The reaction mixture was refluxed until 15 mLs of water had been collected in the trap. A 16 mm×300 mm Vigreux column was then attached between the reaction flask and the trap and distillation was continued until 100 mLs of octane had been collected by intermittently draining the trap over a period of time of 1.5 hours. The flask was cooled slightly and phenyl nonanoate (428.5 g; 1.38 mol) was added to the flask and the remaining octane was removed by distillation. The resulting mixture was refluxed over the Dean-Stark trap at a pot temperature of 292° C. and an overhead temperature between 180° and 282° C., inclusive. The trap was occasionally drained to remove phenol. After four hours at reflux, approximately 70 mLs of phenol and approximately 60 mLs of hexadecane were collected. At the end of the four-hour period, the pot temperature was 301° C. and the overhead temperature fluctuated between 275° and 282° C.

The mixture was cooled and the solid was collected by filtration and washed on the filter with approximately 100 mLs of octane. The filter cake was reslurried in approximately 400 mLs of a mixture of hexane and diethyl ether, collected and then reslurried a second time in approximately 400 mLs of a mixture of pentane and diethyl ether. The remaining solid was collected by vacuum filtration, washed with pentane and dried in an oven at 90° C. to give 214.5 g of a white solid. Analysis by cationic titration indicated that the product consisted of 86.9 weight percent benzenesulfonic acid, 4-hydroxynonanoate, sodium salt. Analysis by NMR indicated that the product also contained 2.8% by weight disodium phenol-2,4-disulfonate with the remainder of the product consisting of sodium 4-hydroxybenzenesulfonic acid.

EXAMPLE 3

Preparation of Benzenesulfonic acid, 4-hydroxy-,heptanoate, sodium salt

A 200 mL, 3-necked round bottom flask equipped with a magnetic stirrer, thermocouple well and a 12 inch fractionating column equipped with a Dean-Stark trap was charged with sodium 4-hydroxybenzenesulfonate dihydrate (19.5 g; 0.084 mol), phenyl heptanoate (47.6 g; 0.231 mol), 45 mLs of octane and 20 mLs of tetradecane. The reaction mixture was heated to reflux and octane and water were removed by draining the trap. The reaction temperature reached 265° C. after all of the octane had been removed. The reaction mixture was heated for 2 hours at a pot temperature of 265°–267° C. (overhead temperature 190°–248° C.) and approximately 6.2 g of phenol was collected in the trap. An additional 20 mLs of tetradecane were added to the flask and the reaction mixture was heated at reflux for an additional 2.5 hours during which time an additional 3.6 g of phenol were collected. Refluxing was continued for another 2 hours, during which time 20.5 g of tetradecane was collected. The reaction mixture was cooled and the solid was collected by vacuum filtration and washed three times each time with approximately 150 mLs of diethyl ether. Analysis of the white product by cationic titration indicated that it contained 88.2 weight percent benzenesulfonic acid, 4-hydroxy-,heptanoate, sodium salt.

A sample of the reaction product was refluxed with methanol and a trace amount of sulfuric acid. Analysis of the resulting methyl ester by VPC showed that the solid contained 3.01 milliequivalents (93 weight percent) benzenesulfonic acid, 4-hydroxy-,heptanoate,-sodium salt.

In a similar manner, several other runs were carried out in which the reactants, solvent and reaction conditions were varied. The results are given in the table below.

TABLE

| | Acyloxybenzenesulfonate Salt Preparation | | | | | |
|---|---|---|---|---|---|---|
| Run No. | Aryl Ester Reactant (g-mol) | Sodium 4-Hydroxybenzene Sulfonate Reactant (g-mol) | Solvent (grams) | Temperature (°C.) | Time (hrs.) | Product (wt. %) |
| 4 | phenyl nonanoate 0.104 | 0.050 | hexadecane (7); dodecane (6) | 278–290 | 5 | benzenesulfonic acid, 4-hydroxy-,nonanoate, sodium salt - 74.7% |
| 5 | phenyl nonanoate 0.079 | 0.036 | tetradecane (21) | 270 | 10.5 | benzenesulfonic acid, 4-hydroxy-,nonanoate, sodium salt - 90% |
| 6 | phenyl nonanoate 0.141 | 0.036 | hexadecane (7) | 301–290 | 2 | benzenesulfonic acid, 4-hydroxy-,nonanoate, sodium salt - 90% |
| 7 | phenyl nonanoate 0.037 | 0.022 | hexadecane (23) | 280–300 | 1–5 | benzenesulfonic acid, 4-hydroxy-,nonanoate, sodium salt - 70% |
| 8 | phenyl nonanoate 0.122 | 0.043 | hexadecane (9) | 290–302 | 1 | benzenesulfonic acid, 4-hydroxy-,nonanoate, sodium salt - 90% |
| 9 | phenyl nonanoate 0.045 | 0.036 | tetradecane (20); hexadecane (18) | 275–280 | 18 | benzenesulfonic acid, 4-hydroxy-,nonanoate, sodium salt - 87% |
| 10 | phenyl nonanoate 0.92 | 0.43 | hexadecane (90) | 288–296 | 2.5 | benzenesulfonic acid, 4-hydroxy-,nonanoate, sodium salt - 85% |
| 11 | phenyl heptanoate 0.087 | 0.025 | hexadecane (12) | 270–280 | 2.5 | benzenesulfonic acid, 4-hydroxy-,heptanoate, sodium salt - 83% |

TABLE-continued

| | | Acyloxybenzenesulfonate Salt Preparation | | | | |
|---|---|---|---|---|---|---|
| Run No. | Aryl Ester Reactant (g-mol) | Sodium 4-Hydroxybenzene Sulfonate Reactant (g-mol) | Solvent (grams) | Temperature (°C.) | Time (hrs.) | Product (wt. %) |
| 12 | phenyl heptanoate 0.189 | 0.058 | tetradecane (22) | 265 | 5 | benzenesulfonic acid, 4-hydroxy-,heptanoate, sodium salt - 87% |
| 13 | phenyl heptanoate 0.170 | 0.045 | NONE | 280 | 1.5 | benzenesulfonic acid, 4-hydroxy-,heptanoate, sodium salt - 85% |
| 14 | phenyl heptanoate 0.189 | .078 | tetradecane (35); mineral oil (15) | 260–280 | 6 | benzenesulfonic acid, 4-hydroxy-,heptanoate, sodium salt - 86% |
| 15 | phenyl nonanoate 0.19 | 0.077 | hexadecane (24) | 294–297 | 7 | benzenesulfonic acid, 4-hydroxy-,nonanoate, sodium salt - 92% |
| 16 | phenyl heptanoate 0.12 | 0.039 | tetraglyme (40); tetradecane (19) | 268 | 4 | benzenesulfonic acid, 4-hydroxy-,heptanoate, sodium salt - 84% |
| 17 | phenyl heptanoate 0.19 | 0.086 | tetradecane (38) | 261 | 23 | benzenesulfonic acid, 4-hydroxy-,heptanoate, sodium salt - 86% |
| 18 | phenyl heptanoate 0.19 | 0.053 | Sulfolane (50); tetradecane (42) | 265 | 18 | benzenesulfonic acid, 4-hydroxy-,heptanoate, sodium salt - 80% |
| 19 | phenyl heptanoate 1.31 | 0.75 | tetradecane (140) | 262 | 12 | benzenesulfonic acid, 4-hydroxy-,heptanoate, sodium salt - 82% |
| 20 | phenyl heptanoate 1.38 | 0.75 | tetradecane (140) | 262 | 9 | benzenesulfonic acid, 4-hydroxy-,heptanoate, sodium salt - 84% |
| 21 | phenyl heptanoate 1.73 | 0.75 | hexadecane (232); mineral oil (77) | 265–271 | 8.5 | benzenesulfonic acid, 4-hydroxy-,heptanoate, sodium salt - 87% |
| 22 | phenyl heptanoate 0.23 | .09 | hexadecane (38) | 263 | 5.5 | benzenesulfonic acid, 4-hydroxy-,heptanoate, sodium salt - 86% |
| 23 | 3,5,5-trimethyl-hexanoate - 0.33 | 0.089 | hexadecane (19) | 278–286 | 4 | benzenesulfonic acid, 4-hydroxy-,3,5,5-tri-methylhexanoate, sodium salt - 85% |
| 24 | 3,5,5-trimethyl-hexanoate - 0.27 | 0.086 | tetradecane (35) | 271 | 9.5 | benzenesulfonic acid, 4-hydroxy-,3,5,5-tri-methylhexanoate, sodium salt - 90% |
| 25 | 3,5,5-trimethyl-hexanoate - 0.27 | 0.087 | tetradecane (10); hexadecane (27) | 284 | 5 | benzenesulfonic acid, 4-hydroxy-,3,5,5-tri-methylhexanoate, sodium salt - 87% |
| 26 | phenyl heptanoate (0.11) phenyl nonanoate (0.11) | 0.088 | tetradecane (26) | 270 | 4.5 | a mixture of: benzenesulfonic acid, 4-hydroxy-,heptanoate, sodium salt and benzenesulfonic acid, 4-hydroxy-,nonanoate, sodium salt - 90% |

Having disclosed the process of the present invention, one skilled in the art can readily envision various modifications and changes which are nevertheless within the scope of the invention. Therefore, it is desired that the process of this invention be limited only by the lawful scope of the appended claims.

We claim:

1. A process for the preparation of an alkali metal or an alkaline earth metal salt of an acyloxybenzenesulfonic acid which comprises reacting at elevated temperature in the range of about 200° to about 350° C. the corresponding hydroxybenzenesulfonate salt with an aryl ester of an aliphatic carboxylic acid.

2. A process for the preparation of an alkali metal or an alkaline earth metal salt of an acyloxybenzenesulfonic acid of the formula:

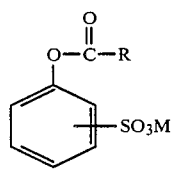

wherein R is a hydrocarbyl group containing up to 30 carbon atoms selected from alkyl, alkenyl, cycloalkyl, aryl, aralkyl and M is an alkali metal or an alkaline earth metal which comprises reacting at elevated temperature in the range of about 200° to about 350° C. the corresponding hydroxybenzene sulfonate salt of the formula:

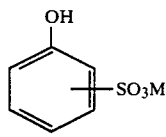
(II)

with an aryl ester of the formula:

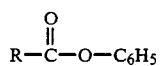
(III)

wherein R is as defined above.

3. The process of claim 2 wherein compounds having the general structural formula (I) are selected from benzenesulfonic acid, 4-hydroxy-,heptanoate,sodium salt; benzenesulfonic acid, 4-hydroxy-,nonanoate,-sodium salt and mixtures thereof.

4. The process of claim 2 wherein the molar ratio of aryl ester reactant to hydroxybenzenesulfonate salt reactant is from about 1.25 to 5:1.

5. The process of claim 2 wherein said process is conducted under substantially anhydrous conditions.

6. The process of claim 2 wherein said reaction is carried out in the presence of a solvent which is inert under the reaction conditions.

7. The process of claim 6 wherein said solvent is a high boiling alkane having from 10 to about 20 carbon atoms.

8. The process of claim 7 wherein said alkane is selected from decane, undecane, tetradecane, hexadecane, mineral oil and mixtures thereof.

9. The process of claim 6 wherein said solvent is an aprotic solvent.

10. The process of claim 9 wherein said aprotic solvent is selected from triglyme, tetraglyme and 1,2-diethoxyethane.

11. The process of claim 6 wherein said solvent is a dipolar aprotic solvent.

12. The process of claim 11 wherein said dipolar aprotic solvent is selected from N,N-dimethylacetamide, tetramethylenesulfone and N-methylpyrrolidinone.

13. A process of claim 2 comprising heating a mixture of (a) said hydroxy benzene sulfonate salt (II) wherein M is an alkali metal and (b) said aryl ester (III) while distilling phenol from the reaction mixture.

14. A process of claim 13 wherein said aryl ester (III) is phenyl heptanoate.

15. A process of claim 13 wherein said aryl ester (III) is phenyl nonanoate.

16. A process of claim 14 wherein said reaction temperature is about 250°–325° C.

17. A process of claim 15 wherein said reaction temperature is about 250°–325° C.

18. A process of claim 13 conducted in the presence of an inert liquid reaction media.

19. A process of claim 18 wherein said inert liquid has a boiling point above phenol and below said aryl ester (III).

20. A process of claim 19 wherein said inert liquid is a high boiling alkane.

* * * * *